United States Patent [19]

Fujino et al.

[11] 4,229,438
[45] Oct. 21, 1980

[54] NONAPEPTIDES

[75] Inventors: Masahiko Fujino, Takarazuka; Osamu Nishimura, Toyonaka; Muneo Takaoki, Kyoto, all of Japan

[73] Assignee: Takeda Chemical Industries, Ltd., Osaka, Japan

[21] Appl. No.: 36,988

[22] Filed: May 7, 1979

[30] Foreign Application Priority Data

May 12, 1978 [JP] Japan .................................. 53/57007

[51] Int. Cl.² ..................... A61K 37/00; C07C 103/52
[52] U.S. Cl. ............................ 424/177; 260/112.5 R; 260/112.5 LH
[58] Field of Search .................................. 260/112.5 R

[56] References Cited

U.S. PATENT DOCUMENTS 4,098,777   7/1978   Veber et al. .................. 260/112.5 R

OTHER PUBLICATIONS

J. Marie Pleau, et al., J. of Biological Chem. 252, 1977, pp. 8045–8047.

*Primary Examiner*—Delbert R. Phillips
*Attorney, Agent, or Firm*—Wenderoth, Lind & Ponack

[57] ABSTRACT

Novel nonapeptides of the formula:

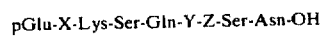

pGlu-X-Lys-Ser-Gln-Y-Z-Ser-Asn-OH wherein X is Ala or (D)-Ala; Y and Z are the same or different and each is the residue of a D-amino acid containing 3 to 9 carbon atoms, or Gly; and at least one of X, Y and Z is the residue of D-amino acid, have immunoregulator activity and are of value as medicines.

11 Claims, No Drawings

NONAPEPTIDES

This invention relates to new nonapeptides which are of value as medicines.

Recently Bach et al [J. M. Pleau, M. Dardenne, Y. Blouquit and J. F. Bach, J. Biol. Chem. 252, 8045 (1977)] isolated from porcine serum a peptide of suspected thymic origin (FTS) which has immunoregulator activity, and has established its chemical structure as pGlu-Ala-Lys-Ser-Gln-Gly-Gly-Ser-Asn-OH. However, it is very difficult to isolate this substance from the blood and put it to medicinal use, because the substance occurs in very small amounts and requires a complicated purification procedure. The present inventors studied the possibility of producing this compound on a mass production scale through the technique of peptide synthesis and, in the course of the study, succeeded in the synthesis of a class of new compounds having strong immunoregulator activity.

Their further research ensued, leading to this invention which comprises: a new nonapeptide of the general formula:

  (I)

pGlu-X-Lys-Ser-Gln-Y-Z-Ser-Asn-OH wherein X means the residue of L- or D-alanine; Y and Z are the same or different and each is the residue of D-amino acid containing 3 to 9 carbon atoms or the residue of glycine; and at least one of X, Y and Z is the residue of D-amino acid.

Throughout this specification, amino acids or amino acid residues, peptides, protective groups, reagents, etc. are sometimes referred to by the abbreviations either adopted by the Committee on Chemical Nomenclature of IUPACIUB or those commonly used in this field of art. Some of such abbreviations are as follows.

Ala: Alanine
Asp: Aspartic acid
Asn: Asparagine
Glu: Glutamic acid
Gln: Glutamine
pGlu: Pyroglutamic acid
Gly: Glycine
Leu: Leucine
Lys: Lysine
Ser: Serine
Phe: Phenylalanine
Val: Valine
Boc: t-Butoxycarbonyl
Cbz: Benzyloxycarbonyl
But: t-Butyl
Bzl: Benzyl
DCC: N,N'-dicyclohexylcarbodiimide
HONB: N-hydroxy-5-norbornene-2,3-dicarboxiimide
ONB: N-hydroxy-5-norbornene-2,3-dicaboxyimide ester
OSu: N-hydroxy-succinimide ester
DMF: Dimethylformamide In this specification, the term 'amino acid residue' means a group capable of forming a peptide bond, i.e. the amino or imino group of an amino acid minus a hydrogen atom and/or the carboxyl group thereof minus a hydroxyl group, and for convenience sake, such an amino acid residue is represented by the above abbreviation for the corresponding amino acid. When an amino acid or amino acid residue is designated by such an abbreviation, unless otherwise indicated, it means the L-form thereof, while any reference to the D-form is accompanied by a prefix representing the same form.

Referring, now, to the above general formula (I), the residue of a D-amino acid of 3 to 9 carbon atoms as represented by Y or Z may for example be the residue of D-form of a neutral amino acid such as alanine, leucine, isoleucine, phenylalanine, valine, 2-amino-n-butyric acid, serine, threonine, norleucine, methionine, norvaline or tyrosine. Among them, particularly as Y, a residue of alanine, leucine, phenylalanine, valine, etc. are preferred and, as Z, alanine, leucine, phenylalanine, valine, etc. are desirable.

The novel nonapeptide (I) according to this invention is produced by deprotecting a protected peptide such that at least one of its constituent amino acid residues of nonapeptide (1) has been protected. The above protected peptide may be represented by the following formula (II), for instance.

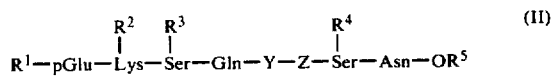

wherein X, Y and Z have the meanings respectively defined hereinbefore; $R^1$ and $R^2$, respectively, mean an amino-protecting group; $R^3$ and $R^4$, respectively, mean a hydroxyl-protecting group; $R^5$ means a carboxyl-protecting group; no protective groups other than $R^2$ is essential.

As the above various protective groups, there may be mentioned the hitherto-known protective groups normally used for protecting amino, hydroxyl and carboxyl groups, respectively. Thus, the amino-protecting groups $R^1$ and $R^2$ may for example be benzyloxycarbonyl, t-butoxycarbonyl, t-amyloxycarbonyl, isobornyloxycarbonyl, adamantyloxycarbonyl, o-nitrophenylthio, diphenylphosphinothioyl, chloro- or nitrobenzyloxycarbonyl or the like. The hydroxyl-protecting groups $R^3$ and $R^4$ may for example be benzyl, t-butyl or the like (in the form of an ether). As exemplary carboxyl-protecting groups $R^5$, there may be mentioned benzyl, chloro-, bromo- or nitro-benzyl or t-butyl (in the form of an ester.) It should be understood that $R^5$ may represent a resin for the solid-phase synthesis process. Depending on the peptide synthesis process used, none of the above-mentioned protective groups other than $R^2$ is absolutely essential and the protective groups $R^1$, $R^3$ and $R^5$ need not be present at all.

The deprotecting procedure to be used in the method of this invention may be the per se known reductive cleavage reaction or acid cleavage reaction.

The reductive cleavage reaction procedure may for example be hydrogenolysis with the aid of palladium black, palladium-on-carbon, platinum or other catalyst or a reduction reaction involving the use of sodium metal in liquid ammonia.

The acid to be used in said acid cleavage reaction may for example be methanesulfonic acid, trifluoroacetic acid, hydrochloric acid or hydrogen fluoride. In the acid cleavage reaction, it is sometimes advantageous to add a cation acceptor such as anisole, phenol or thioanisole. The removal of protective groups by such reduction or acid cleavage reaction may normally be effected at a reaction temperature from about $-20°$ C. to about $+40°$ C.

What deprotecting procedure to follow depends upon the type of protective groups on the protected nonapeptide (II) but since it should be commercially advantageous to ensure that all the existing protective groups will be removed in a single step, this possibility should be explored when selecting the protective groups to be employed.

The following table shows typical combinations of protective groups and deprotecting conditions.

TABLE 1

| Conditions of deprotecting reaction | Combinations of protective groups and deprotecting conditions |||||
|---|---|---|---|---|---|
| | Protective group ||||| 
| | $R^1$ | $R^2$ | $R^3$ | $R^4$ | $R^5$ |
| $H_2/Pd$ | Cbz | Cbz | Bzl | Bzl | Bzl |
| HF | | | | | |
| $CH_3SO_3H$ | — | Cbz | — | — | Bzl |
| HF | Cbz | Cbz | Bzl | Bzl | Ⓟ |
| $CF_3COOH$ | Boc | Boc | Bu$^t$ | Bu$^t$ | Bu$^t$ |
| $CF_3COOH$ | — | Boc | — | — | Bu$^t$ |
| $H_2/Pd$ | — | Cbz | — | — | Bzl(Cl) |

In the above table, P denotes a resin for solid-phase synthesis; Bzl(Cl) denotes p-chlorobenzyl.

It should be noted that the protected nonapeptide (II) for use in the method of this invention can be produced from the constituent amino acids or/and peptide fragments by the per se known peptide synthesis procedure.

The nonapeptide (I) produced in accordance with this invention can be isolated and purified from the reaction mixture by the established peptide isolation procedures (e.g. extraction, distribution, precipitation or column chromatography). If required, the nonapeptide (I) can be obtained in the form of a salt with an organic acid (e.g. citric acid, tartaric acid or succinic acid) or a mineral acid (e.g. hydrochloric acid, hydrobromic acid or sulfuric acid), or in the form of a salt with a metal (e.g. zinc, aluminum or iron). While such salts of course fall within the scope of this invention, it is normally advantageous to isolate the peptide in its free form or as the acetate and in many of such cases the product is obtained as the hydrate.

The nonapeptide (I) according to this invention acts on the precurser of T cells (thymus-derived lymphocytes) to promote their differentiation into subpopulations of functionally active T cells such as helper T cells, suppressor T cells and effector T cells of cell mediated immunity. These T lymphocytes display their functions while interferring with each other and thereby augment the overall immunological competence of the host. Therefore, the nonapeptide (I) with such immunoregulator activity is of value as a therapeutic or life extending drug for administration to mammalian animals (e.g. the human being, cattle, rabbit, guinea pig or mouse) with such diseases as the immunodeficiency diseases caused by a functional abnormality of the thymus (e.g. Di George's syndrome, IgA deficiency or the immunological deffficiencies accompanying ataxia telangiectasia), autoimmune diseases (e.g. rheumatic fever, systemic lupus erythematosus, chronic rheumatoid arthritis, progressive systemic screrosis, dermatomycositis, periarteritis nodosa, Behcet's disease, Sjögren's syndrome, or the immunodepression at the terminal stage of cancer); as a drug for mitigating the immunological incompetence of the host body which may be encountered as a side effect of anticancer medication; or as a drug for mitigating the untoward effects of immunosuppressive therapies. The nonapeptide (I) is important also as a drug for the prophylaxis of an immunological alteration, i.e. a weakened defense mechanism of the host against infections, which is consequential to senility or various diseases.

When the nonapeptide (I) of this invention is used for the above medicinal use, it can be safely administered parenterally or orally, either as it is or as formulated with an appropriate pharmacologically acceptable carrier, excipient or diluent and in such dosage forms as injections, suppositories, powders, capsules, etc. Normally to avoid the influence of the digestive tract, the nonapeptide (I) is preferably administered by routes other than oral, e.g. injection or rectal and vaginal administration. An injectable solution, for instance, may be prepared by dissolving about 1 $\mu$g to 10 mg of peptide (I) in 1 to 5 ml of physiological saline. It is also possible to prepare a lyophilized ampoule preparation using mannitol, sorbitol or the like as a volume builder for extemporaneous administration.

The proper dosage of peptide (I) as a medicament depends, of course, on such factors as the disease to be managed, the condition of the case and the route of administration. However, in view of its low toxicity, the nonapeptide (I) can be administered to a man or a mouse, for instance, at a suitable dose within the range of about 1 ng to 10 mg, preferably 20 $\mu$g to 600 $\mu$g, daily per kilogram body weight by routes other than oral, e.g. intravenously or subcutaneously.

The immunoregulator activity of the nonapeptide (I) according to this invention can be demonstrated by assaying its theta antigen induction activity in connection with the differentiation of thymocytes into differently functional T cells.

DETERMINATION OF THETA ANTIGEN INDUCTION ACTIVITY

The theta antigen induction activity of the nonapeptide (I) is assayed by a procedure analogous to the procedure described in the article of Komuro et al [The Lancet, i, 740–743 (1973)].

The spleen is enucleated from a C3H/He mouse, 2–3 months old, and minced in a tissue culture fluid (RPMI-1640). The resulting spleen cell suspension is fractionated by discontinuous density gradient centrifugation using 10 to 35% bovine serum albumin. The cells migrating to the 23–26% albumin layer interface are collected and resuspended in RPMI-1640. To this cell suspension is added the peptide, the activity of which is to be determined, at a varying concentration and the mixture is incubated at 37° C. for 2 hours. If the peptide added be active, fresh theta antigen will appear on the cell surface. Therefore, the count of such cells is taken by lysing with an outbred mouse anti(theta) serum and guinea-pig complement. The theta-antigen induction activity is computed by means of the following equation. Theta-antigen induction activity(%)=(A−B/A)×100 where A is the count of theta antigen-negative cells in the absence of the test peptide and B is the count of theta antigen-negative cells when the test peptide has been added.

The activities of some representative peptides of this invention as determined by the above assay method are shown in the following table.

| The peptides of this invention ||| The concentration (ng/ml) required for showing at least 10% theta antigen induction activity |
|---|---|---|---|
| X | Y | Z | |
| D-Ala | Gly | Gly | 1–10 |

-continued

| The peptides of this invention | | | The concentration (ng/ml) required for showing at least 10% theta antigen |
|---|---|---|---|
| X | Y | Z | induction activity |
| Ala | D-Ala | Gly | 0.1-1 |
| Ala | Gly | (D)-Ala | 1-10 |

That the compound of this invention has specific activity is evident from the fact that no such activity is found in structurally very close compounds. By way of example, the above value of the analogous compound where X is (D)-Leu is >1000 ng/ml, the value of the analog where Y is (D)-Ala with the lack of Asn at the C-terminal is >1000 ng/ml and the value of the analog where Z is (D)-Ala with the lack of pGlu at the N-terminal is also >1000 ng/ml, all being virtually equivalent to no activity.

This invention will be described below in further detail by way of examples which should, however, be construed as illustrative and by no means limitative of the invention.

Referring to these examples, the Amberlite IRA-410 used in ion exchange procedures is the product of Rohm and Haas Company and the Sephadex LH-20 used in final purification procedures is the product of Pharmacia AB. The thin-layer chromatographies were carried out with the following solvent systems and, as the carrier, silica gel 60F-254 (Merck, Germany, for $Rf^1$, $Rf^2$, $Rf^6$) or Avicel (Funakoshi Yakuhin, K. K., for $Rf^4$).

$Rf^1$ = chloroform-methanol-acetic acid = 9:1:0.5
$Rf^2$ = ethyl acetate-pyridine-acetic acid-water = 60:20:6:11
$Rf^4$ = n-butanol-pyridine-acetic acid-water = 30:20:6:24
$Rf^6$ = chloroform-methanol-water = 7:3:0.5

EXAMPLE 1

Production of pGlu-(D)-Ala-Lys-Ser-Gln-Gly-Gly-Ser-Asn-OH (I) Production of Cbz-Ser-Asn-OBu$^t$ In 100 ml of methanol is dissolved 4.8 g (15 m mols) of Cbz-Asn-OBu$^t$, and following addition of 0.9 ml acetic acid, catalytic reduction is carried out with palladium black as the catalyst. The catalyst is filtered off, the filtrate concentrated and the residue dissolved in 50 ml of DMF. To this solution is added Cbz-Ser-ONB (prepared from 3.6 g Cbz-Ser-OH and 3.0 g HONB by the DCC process), followed by stirring at room temperature overnight. The DMF is distilled off and the residue is extracted with 200 ml of ethyl acetate. The extract is washed with 5% aqueous sodium hydrogen carbonate and dried over anhydrous $Na_2SO_4$. The ethyl acetate is then distilled off and the resulting crystals are collected by filtration and recrystallized from ethyl acetate-petroleum benzin. Yield 4.8 g (78%); m.p. 111°-112° C.; $[\alpha]_D^{23}$ −14.5° (c=1.0, MeOH); $Rf^1$=0.42.

Elemental analysis, for $C_{19}H_{27}O_7N_3$; Calcd. C, 55.73; H, 6.65; N, 10.26. Found C, 55.92; H, 6.86; N, 10.10.

(II) Production of Cbz-Gly-Ser-Asn-OBu$^t$

In 100 ml of methanol is dissolved 7.8 g (19 m mols) of Cbz-Ser-Asn-OBu$^t$, and following addition of 1.2 ml acetic acid, catalytic reduction is carried out with palladium black as the catalyst. The catalyst is filtered off, the methanol distilled off and the residue dissolved in 50 ml of DMF. To this solution is added 7.0 g (19 m mols) of Cbz-Gly-ONB, followed by stirring at room temperature overnight. The DMF is then distilled off and the residue is extracted with a solvent mixture of n-butanol (50 ml) and ethyl acetate (100 ml), followed by washing with a 5% aqueous solution of sodium hydrogen carbonate. The solvent is distilled off and the resulting crystals are recovered by filtration. Yield 8.5 g (96%); m.p. 144°-145° C. $[\alpha]_D^{23}$ −10.6° (c=0.5, DMF); $Rf^1$=0.31.

Elemental analysis, for $C_{21}H_{30}O_8N_4$; Calcd. C, 54.07; H, 6.48; N, 12.01. Found C, 53.78; H, 6.67; N, 11.75.

(III) Production of Cbz-Ser-Gln-Gly-OH

To 35 g of Cbz-Ser-Gln-Gly-OBu$^t$ is added 220 ml of trifluoroacetic acid and the mixture is shaken at room temperature for 35 minutes. The trifluoroacetic acid is distilled off under reduced pressure, the residue is treated with 500 ml of ether and the resulting powders are collected by filtration, dried and recrystallized from 200 ml of methanol. Yield 26.1 g (81.0%); m.p. 203°-204° C.; $[\alpha]_D^{21}$ +3.1° (c=1.10, DMF); $Rf^2$=0.15.

Elemental analysis, for $C_{18}H_{24}O_8N_4 \cdot H_2O$; Calcd. C, 48.86; H, 5.92; N, 12.66. Found: C, 48.76; H, 5.85; N, 12.47.

(IV) Production of Cbz-Ser-Gln-Gly-Gly-Ser-Asn-OBu$^t$

In 150 ml of methanol is dissolved 7.85 g (0.015 mol) of Cbz-Gly-Ser-Asn-OBu$^t$, and following addition of 0.9 ml (0.015 mol) of acetic acid, catalytic reduction is carried out in the presence of palladium black. The catalyst is filtered off, 2.30 ml of 6.51 N-HCl (in dioxane) is added to the filtrate and the solvent is distilled off under reduced pressure. The residue is dissolved in 20 ml of DMF and under ice-cooling, 1.92 ml (0.015 mol) of N-ethylmorpholine is added. Separately, 6.64 g (0.015 mol) of Cbz-Ser-Gln-Gly-OH and 4.04 g (0.0225 mol) of HONB are dissolved in 20 ml of DMF, 3.39 g (0.0165 mol) of DCC is added under ice-cooling and the mixture is stirred for 12 hours. The byproduct dicyclohexylurea is filtered off and the filtrate is combined with the amine component prepared above. The mixture is stirred at room temperature for 24 hours. To the gel-like reaction mixture is added 300 ml of ethanol and the resulting precipitate is recovered by filtration and recrystallized from methanol. Yield 9.30 g. (83.9%); m.p. 168°-170° C.(decompn.); $[\alpha]_D^{23}$ −11.0°(c=0.67, DMF); $Rf^2$=0.35, $Rf^6$=0.31.

Elemental analysis, for $C_{31}H_{46}O_{13}N_8 \cdot \frac{1}{2}H_2O$; Calcd. C, 49.79; H, 6.34; N, 14.99. Found C, 49.71; H, 6.34; N, 14.69.

(V) Production of Cbz-Lys(Boc)-Ser-Gln-Gly-Gly-Ser-Asn-OBu$^t$

In 150 ml of a 7:3 mixture of ethanol and water is dissolved 8.86 g (0.012 mol) of Cbz-Ser-Gln-Gly-Gly-Ser-Asn-OBu$^t$, and following addition of 0.72 ml glacial acetic acid, catalytic reduction is carried out with palladium black as in the usual manner. The catalyst is filtered off, 2.0 ml of 6N-HCl is added to the filtrate and the solvent is distilled off under reduced pressure. The residue is suspended in 30 ml of DMF and a dioxane solution of Cbz-Lys(Boc)-ONB[prepared from 7.08 g (0.0126 mol) of Cbz-Lys-(Boc)-OH.DCHA, 2.26 g (0.0126 mol) of HONB and 2.60 g (0.0126 mol) of DCC] is added to the suspension. The mixture is stirred at room temperature for 48 hours. To this reaction mixture is added 350 ml of ethanol and the resulting precipitate is collected by filtration and recrystallized from ethanol. Yield 10.0 g (86.2%); m.p. 185°-186° C.(decompn.); $[\alpha]_D^{25}$ −11.4°(c=0.56, DMF); $Rf^2$=0.41, $Rf^6$=0.35.

Elemental analysis, for $C_{42}H_{66}O_{16}N_{10} \cdot H_2O$; Calcd. C, 51.21; H, 6.96; N, 14.22. Found C, 51.30; H, 6.98; N, 14.14.

(VI) Production of Cbz-(D)-Ala-Lys(Boc)-Ser-Gln-Gly-Gly-Ser-Asn-OBu$^t$

In 100 ml of 10% aqueous methanol is dissolved 800 mg (0.83 m mol) of Cbz-Lys-(Boc)-Ser-Gln-Gly-Gly-Ser-Asn-OBu$^t$ and following addition of 0.05 ml acetic acid, catalytic reduction is carried out with palladium black as the catalyst. The catalyst is filtered off and the filtrate is concentrated under reduced pressure. The residue is dissolved in 10 ml of DMF and Cbz-(D)-Ala-ONB [prepared from 200 mg of Cbz-(D)-Ala-OH and 177 mg of HONB by the DCC process] is added to the solution. The mixture is stirred at room temperature overnight. The DMF is distilled off and the residue is precipitated with ethanol and recovered by filtration. Yield 750 mg; m.p. 192°–193° C. (decompn.); $[\alpha]_D^{25} -23.4°(c=0.5, 50\%$ acetic acid); Rf$^2$=0.58.

Elemental analysis, for $C_{45}H_{71}O_{17}N_{11} \cdot \frac{1}{2}H_2O$; Calcd. C, 51.61; H, 7.69; N, 14.71. Found C, 51.59; H, 7.12; N, 14.42.

(VII) Production of pGlu-(D)-Ala-Lys(Boc)-Ser-Gln-Gly-Gly-Ser-Asn-OBu$^t$

In 100 ml of aqueous methanol is dissolved 380 mg (0.38 m mol) of Cbz-(D)-Ala-Lys(Boc)-Ser-Gln-Gly-Gly-Ser-Asn-OBu$^t$ and catalytic reduction is carried out with palladium black as the catalyst. The catalyst is filtered off, the solvent is distilled off and the residue is dissolved in 10 ml of DMF. To this solution is added pGlu-ONB (prepared from 58 mg of pGlu-OH and 95 mg of HONB by DCC process), followed by stirring, whereupon a gel is formed. This reaction mixture is precipitated with ethanol and recovered by filtration. Yield 299 mg (78%); m.p. 201°–202° C. (decompn.); $[\alpha]_D^{22} -17.9°(c=0.33, 50\%$ acetic acid); Rf$^2$=0.18.

Elemental analysis, for $C_{42}H_{70}O_{17}N_{12} \cdot \frac{1}{2}H_2O$; Calcd. C, 49.25; H, 7.08; N, 16.41. Found C, 49.08; H, 7.07; N, 16.11.

(VIII) Production of pGlu-(D)-Ala-Lys-Ser-Gln-Gly-Gly-Ser-Asn-OH

In 2 ml of trifluoroacetic acid is dissolved 240 mg of pGlu-(D)-Ala-Lys(Boc)-Ser-Gln-Gly-Gly-Ser-Asn-OBu$^t$ and the solution is allowed to stand at room temperature for 60 minutes. The trifluoroacetic acid is distilled off and the residue is precipitated with ether and recovered by filtration. The powders thus obtained are dissolved in 30 ml of water and the solution is passed through a column of Amberlite IRA-410 (acetate-form)(2×4 cm). The effluent is combined with washings and lyophilized. The powdery lyophilizate is dissolved in a small amount of 0.1 N-aqueous acetic acid and put onto a column of Sephadex LH-20 (2.5×125 cm), elution being carried out with 0.1 N-aqueous acetic acid. The fractions from 195 ml through 240 ml are pooled and lyophilized, whereupon 150 mg powders of the indicated compound are obtained. Yield 68%; $[\alpha]_D^{25} -16.6°(c=0.5, 50\%$ acetic acid); Rf$^4$(Avicel)=0.20; amino acid analysis (as hydrolyzed with HCl): Lys, 1.18(1); Asp, 1.00(1); Ser, 1.67(2); Glu, 2.03(2); Gly, 2.09(2); Ala, 0.86(1); average recovery 79%.

EXAMPLE 2

Production of pGlu-(D)-Ala-Lys-Ser-Gln-Gly-(D)-Ala-Ser-Asn-OH (I) Production of Cbz-(D)-Ala-Lys(Boc)-Ser-Gln-Gly-(D)-Ala-Ser-Asn-OBu$^t$ In 50 ml of 10% aqueous methanol is dissolved 422 mg of Cbz-Lys(Boc)-Ser-Gln-Gly-(D)-Ala-Ser-Asn-OBu$^t$ and catalytic reduction is carried out with palladium black as the catalyst. The catalyst is filtered off, 115 mg of Cbz-(D)-Ala-OH is added and the solvent is distilled off. The residue is dissolved in 5 ml of DMF and under cooling at 0° C., 93 mg of HONB and 106 mg of DCC are added. The mixture is stirred at 0° C. for 3 hours and, then at room temperature overnight. The DMF is distilled off and the residue is precipitated with ethanol and reprecipitated with DMF-ethanol. Yield 370 mg (81%); m.p. 228°–230° C.; $[\alpha]_D^{23} -4.7°(c=0.42, 50\%$ acetic acid); Rf$^2$=0.44.

Elemental analysis, for $C_{40}H_{73}O_{17}N_{11} \cdot H_2O$ Calcd. C, 51.62; H, 7.06; N, 14.40. Found C, 51.66; H, 6.94; N, 14.33.

(II) Production of pGlu-(D)-Ala-Lys(Boc)-Ser-Gln-Gly-(D)-Ala-Ser-Asn-OBu$^t$

In 50 ml of 10% aqueous methanol is dissolved 300 mg of Cbz-(D)-Ala-Lys(Boc)-Ser-Gln-Gly-(D)-Ala-Ser-Asn-OBu$^t$ and catalytic reduction is carried out with palladium black as the catalyst. The catalyst is filtered off, 47 mg of pGlu-OH is added to the filtrate and the solvent is distilled off. The residue is dissolved in 5 ml of DMF and under cooling at 0° C., 75 mg of DCC and 71 mg of HONB are added. The mixture is stirred at 0° C. for 3 hours and at room temperature overnight. The DMF is distilled off and the residue is precipitated with ethanol and recovered by filtration. Yield 290 mg (93%); m.p. 195°–196° C. (decompn.); $[\alpha]_D^{23} -6.6°(c=0.29, 50\%$ acetic acid); Rf$^2$=0.12.

Elemental analysis, for $C_{43}H_{72}O_{17}N_{12} \cdot 2H_2O$: Calcd. C, 48.48; H, 7.00; N, 15.78. Found C, 48.13; H, 6.76; N, 15.66.

(III) Production of pGlu-(D)-Ala-Lys-Ser-Gln-Gly-(D)-Ala-Ser-Asn-OH

In 2 ml of trifluoroacetic acid is dissolved 250 mg of pGlu-(D)-Ala-Lys(Boc)-Ser-Gln-Gly-(D)-Ala-Ser-Asn-OBu$^t$ and the solution is allowed to stand at room temperature for 60 minutes. The solvent is distilled off and the residue is precipitated with ether and recovered by filtration. The resulting powders are dissolved in 50 ml of water and passed through a column of Amberlite IRA-410 (acetate-form) (2×5 cm). The effluent is combined with washings and lyophilized. The powdery lyophilizate is dissolved in a small amount of water and put onto a column of Sephadex LH-20 (2.5×125 cm), elution being carried out with 0.1 N-acetic acid. The fractions from 182 ml through 218 ml are pooled and lyophilized. Yield 86 mg (34%); $[\alpha]_D^{23} -6.0°(c=0.25,$ water); Rf$^4$=0.23; amino acid analysis (as hydrolyzed with HCl): Lys, 0.97(1); Asp, 0.97(1); Ser, 1.80(2); Glu, 2.07(2); Gly, 1.00(1); Ala, 1.93(2); average recovery 82%.

EXAMPLE 3

Production of pGlu-Ala-Lys-Ser-Gln-Gly-(D)-Ala-Ser-Asn-OH (I) Production of Cbz-(D)-Ala-Ser-Asn-OBu$^t$ In 100 ml of methanol is dissolved 2.86 g (7 m mols) of Cbz-Ser-Asn-OBu$^t$, and following addition of 0.5 ml of acetic acid, catalytic reduction is carried out with palladium black as the catalyst. The catalyst is filtered off, the methanol is distilled off and the residue is dissolved in 50 ml of DMF. To this solution is added Cbz-(D)-Ala-ONB[prepared from 1.56 g of Cbz-(D)-Ala-OH and 1.38 g of HONB by DCC process] and the mixture is stirred at room temperature overnight. The DMF is distilled off, the residue extracted with 100 ml of ethyl acetate, and the extract washed with 5% aqueous sodium hydrogen carbonate and dried over anhydrous $Na_2SO_4$. The ethyl acetate is distilled off and the resulting crystals are collected by filtration and recrystallized from ethyl acetate. Yield 2.2 g (66%); m.p. 140°–141° C.; $[\alpha]_D^{25} -13.2°(c=0.5, DMF)$; $Rf^1=0.44$.

Elemental analysis, for $C_{22}H_{32}O_8N_4$: Calcd. C, 54.99; H, 6.71; N, 11.66. Found C, 55.34; H, 7.04; N, 11.16.

(II) Production of Cbz-Ser-Gln-Gly-(D)-Ala-Ser-Asn-OBu$^t$

In 100 ml of methanol is dissolved 1.78 g of Cbz-(D)-Ala-Ser-Asn-OBu$^t$ and catalytic reduction is carried out with palladium black as the catalyst. The catalyst is filtered off and 1.63 g of Cbz-Ser-Gln-Gly-OH is added to the filtrate. The methanol is then distilled off, the residue is dissolved in 20 ml of DMF, and under cooling at 0° C., 790 mg of HONB and 840 mg of DCC are added. The mixture is stirred at 0° C. for 3 hours and, then, at room temperature overnight. To the reaction mixture is added 50 ml of water, the insolubles are filtered off, and the filtrate is concentrated. The residue is precipitated with ethanol and collected by filtration. Yield 2.3 g (81%); m.p. 191°–195° C. (decompn.); $[\alpha]_D^{24} -17.6°(c=0.5, 50\%$ acetic acid); $Rf^2=0.48$ Elemental analysis, for $C_{32}H_{48}O_{13}N_8 \cdot H_2O$: Calcd. C, 49.86; H, 6.53; N, 14.54. Found C, 49.99; H, 6.43; N, 14.94.

(III) Production of Cbz-Lys(Boc)-Ser-Gln-Gly-(D)-Ala-Ser-Asn-OBu$^t$

In 100 ml of aqueous methanol is dissolved 2.08 g. (2.7 m mols) of Cbz-Ser-Gln-Gly-(D)-Ala-Ser-Asn-OBu$^t$, and following addition of 0.2 ml acetic acid, catalytic reduction is carried out with palladium black as the catalyst. The catalyst is filtered off and the residue is dissolved in 20 ml of DMF. To this solution is added Cbz-Lys(Boc)-ONB [prepared from 1.69 g of Cbz-Lys(Boc)-OH.DCHA and 590 mg of HONB by the DCC process] and the mixture is stirred at room temperature overnight. The DMF is distilled off and the residue is precipitated with ethanol and collected by filtration. Yield 2.2 g (83%); m.p. 192°–194° C.(decompn.); $[\alpha]_D^{24} -21.4°(c=0.5, 50\%$ acetic acid); $Rf^2=0.53$.

Elemental analysis, for $C_{43}H_{68}O_{16}N_{10} \cdot H_2O$: Calcd. C, 51.69; H, 7.06; N, 14.02. Found C, 51.86; H, 7.14; N, 14.24.

(IV) Production of Cbz-Ala-Lys(Boc)-Ser-Gln-Gly-(D)-Ala-Ser-Asn-OBu$^t$

In 50 ml of 10% aqueous methanol is dissolved 1.37 g (1.4 m mols) of Cbz-Lys(Boc)-Ser-Gln-Gly-(D)-Ala-Ser-Asn-OBu$^t$, and following addition of 0.1 ml acetic acid, catalytic reduction is carried out with palladium black as the catalyst. The catalyst is filtered off, the solvent is distilled off and the residue is dissolved in 10 ml of DMF. To this solution is added Cbz-Ala-ONB [prepared from 344 mg of Cbz-Ala-OH and 301 mg of HONB by the DCC process] and the mixture is stirred at room temperature overnight. The DMF is distilled off and the residue is precipitated with ethanol and recovered by filtration. Yield 1.20 g (82%); m.p. 195°–198° C.(decompn.); $[\alpha]_D^{24} -27.4°(c=0.5, 50\%$ acetic acid); $Rf^2=0.51$.

Elemental analysis, for $C_{46}H_{73}O_{17}N_{11} \cdot H_2O$: Calcd. C, 51.62; H, 7.06; N, 14.40. Found C, 51.68; H, 6.94; N, 14.43.

(V) Production of pGlu-Ala-Lys(Boc)-Ser-Gln-Gly-(D)-Ala-Ser-Asn-OBu$^t$

In 50 ml of 10% aqueous methanol is dissolved 800 mg (0.76 m mol) of Cbz-Ala-Lys(Boc)-Ser-Gln-Gly-(D)-Ala-Ser-Asn-OBu$^t$, and following addition of 0.1 ml acetic acid, catalytic reduction is carried out with palladium black as the catalyst. The catalyst is filtered off, the solvent is distilled off and the residue is dissolved in 5 ml of DMF. To this solution is added pGlu-ONB (prepared from 118 mg of pGlu-OH and 190 mg of HONB by the DCC process) and the mixture is stirred at room temperature overnight. The DMF is distilled off and the residue is precipitated with ethanol and recovered by filtration. Yield 710 mg (91%); m.p. 203°–205° C.; $[\alpha]_D^{24} -33.8°(c=0.5, 50\%$ acetic acid); $Rf^2=0.19$.

Elemental analysis, for $C_{43}H_{72}O_{17}N_{12} \cdot 2H_2O$: Calcd. C, 48.48; H, 7.00; N, 15.78. Found C, 48.22; H, 7.15; N, 15.39.

(V) Production of pGlu-Ala-Lys-Ser-Gln-Gly-(D)-Ala-Ser-Asn-OH

In 5 ml of trifluoroacetic acid is dissolved 500 mg of pGlu-Ala-Lys(Boc)-Ser-Gln-Gly-(D)-Ala-Ser-Asn-OBu$^t$ and the mixture is allowed to stand at room temperature. The trifluoroacetic acid is distilled off and the residue is precipitated with ether and recovered by filtration. The resulting powders are dissolved in 50 ml of water and run onto a column of Amberlite IRA-410(acetate-form) (2×5 cm). The effluent is combined with washings and lyophilized. The powdery lyophilizate is dissolved in a small amount of 0.1 N-aqueous acetic acid and put onto a column of Sephadex LH-20 (2.5×125 cm), elution being carried out with 0.1 N-aqueous acetic acid. The fractions from 186 ml through 206 ml are pooled and lyophilized. Yield 310 mg (62%); $[\alpha]_D^{24} -47.3°(c=0.35, H_2O)$; $Rf^4$ (Avicel)=0.24; amino acid analysis (acid hydrolyzate); Lys, 1.08(1); Asp, 1.00(1); Ser, 1.90(2); Glu, 1.93(2); Gly, 1.06(1); Ala, 2.00(2); average recovery 89%.

EXAMPLE 4

Production of pGlu-Ala-Lys-Ser-Gln-(D)-Ala-Gly-Ser-Asn-OH (I) Production of Cbz-(D)-Ala-Gly-OBu$^t$ In 100 ml of tetrahydrofuran are dissolved 6.7 g (30 m mols) of Cbz-(D)-Ala-OH and 4.3 g (33 m mols) of H-Gly-OBu$^t$, and under cooling at 0° C., 5.9 g of HONB and 6.8 g of DCC are added. The mixture is stirred overnight, the precipitated urea derivative is filtered off and the tetrahydrofuran is distilled off. The residue is extracted with 200 ml of ethyl acetate, washed with 5% aqueous sodium hydrogen carbonate and dried over anhydrous sodium sulfate. The ethyl acetate is distilled off and the residue is crystallized with petroleum benzin and recrystallized from ethyl acetate-petroleum benzin. Yield 8.2 g (82%); m.p. 77°–78° C.; $[\alpha]_D^{24} +22.6°(c=1.0, MeOH)$.

Elemental analysis, for $C_{17}H_{24}O_5N_2$: Calcd. C, 60.70; H, 7.19; N, 8.33. Found C, 61.00; H, 7.02; N, 8.04.

(II) Production of Cbz-Gln-(D)-Ala-Gly-OBu$^t$

In 100 ml of methanol is dissolved 3.36 g (10 m mols) of Cbz-(D)-Ala-Gly-OBu$^t$ and catalytic reduction is carried out with palladium black as the catalyst. The catalyst is filtered off, the methanol is distilled off and the residue is dissolved in 30 ml of DMF. To this solution is added Cbz-Gln-ONB (prepared from 2.8 g of Cbz-Gln-OH and 1.97 g of HONB by the DCC process) and the mixture is stirred at room temperature overnight. The DMF is distilled off and the residue is precipitated with ether, recovered by filtration and recrystallized from ethyl acetate. Yield 3.10 g (67%); m.p. 194°–195° C.; $[\alpha]_D^{24}+5.8°(c=0.5, DMF)$, $Rf^1=0.58$.

Elemental analysis, for $C_{22}H_{32}O_7N_4$: Calcd. C, 56.88; H, 6.94; N, 12.06. Found C, 56.76; H, 7.19; N, 11.86.

(III) Production of Cbz-Ser-Gln-(D)-Ala-Gly-OBu$^t$

In 200 ml of methanol is dissolved 2.55 g (5.5 m mols) of Cbz-Gln-(D)-Ala-Gly-OBu$^t$ and catalytic reduction is carried out with palladium black as the catalyst. The catalyst is filtered off, the methanol is distilled off and the residue is dissolved in 50 ml of DMF. To this solution is added Cbz-Ser-ONB(prepared from 1.32 g of Cbz-Ser-OH and 1.1 g of HONB by the DCC process) and the mixture is stirred at room temperature overnight. The DMF is distilled off and the residue is precipitated with ether, recovered by filtration and reprecipitated from methanol-ether. Yield 2.95 g (97%); m.p. 190°–192° C. (decompn.); $[\alpha]_D^{27}-6.2°(c=0.5, 50\%$ acetic acid), $Rf^1=0.31$ Elemental analysis, for $C_{25}H_{37}O_9N_5 \cdot \frac{1}{2}H_2O$: Calcd. C, 53.56; H, 6.83; N, 12.49. Found C, 53.37; H, 6.67; N, 12.33.

(IV) Production of Cbz-Ser-Gln-(D)-Ala-Gly-OH

In 20 ml of trifluoroacetic acid is dissolved 2.1 g (3.8 m mols) of Cbz-Ser-Gln-(D)-Ala-Gly-OBu$^t$ and the solution is allowed to stand at room temperature for 40 minutes. The trifluoroacetic acid is distilled off and the residue is precipitated with ether, collected by filtration and dried. It is then washed by boiling with ethanol. Yield 1.6 g (85%); m.p. 189°–190° C. (decompn.); $[\alpha]_D^{27}-12.2°(c=0.5, 50\%$ acetic acid; $Rf^1=0.23$.

Elemental analysis, for $C_{21}H_{29}O_9N_5 \cdot H_2O$: Calcd. C, 49.12; H, 6.09; N, 13.64. Found C, 49.51; H, 5.97; N, 13.57.

(V) Production of Cbz-Ser-Gln-(D)-Ala-Gly-Ser-Asn-OBu$^t$

In 100 ml of methanol is dissolved 1.24 g (3 m mols) of Cbz-Ser-Asn-OBu$^t$ and catalytic reduction is carried out with palladium black as the catalyst. The catalyst is filtered off, Cbz-Ser-Gln-(D)-Ala-Gly-OH is added to the filtrate and the methanol is distilled off. The residue is dissolved in 60 ml of DMF, and under cooling at 0° C., 536 mg of HONB and 619 mg of DCC are added. The mixture is stirred at 0° C. for 3 hours and at room temperature overnight. To this reaction mixture is added 10 ml of water, the insolubles filtered off and the solvent distilled off. The residue is precipitated with ethanol and recovered by filtration. Yield 1.65 g (87%); m.p. 196°–197° C. (decompn.); $[\alpha]_D^{27}-28.6°(c=0.5, 50\%$ acetic acid); $Rf^2=0.48$.

Elemental analysis, for $C_{32}H_{48}O_{13}N_8 \cdot \frac{1}{2}H_2O$: Calcd. C, 50.45; H, 6.48; N, 14.71. Found C, 50.36; H, 6.68; N, 14.59.

(VI) Production of Cbz-Lys(Boc)-Ser-Gln-(D)-Ala-Gly-Ser-Asn-OBu$^t$

In 10% aqueous methanol is dissolved 1.5 g (2 m mols) of Cbz-Ser-Gln-(D)-Ala-Gly-Ser-Asn-OBu$^t$ and catalytic reduction is carried out with palladium black as the catalyst.

The catalyst is filtered off, the filtrate concentrated and the residue dissolved in 20 ml of DMF. To this solution is added Cbz-Lys(Boc)-ONB [prepared from 1.2 g of Cbz-Lys(Boc)-OH.DCHA and 420 mg of HONB by the DCC process] and the mixture is stirred at room temperature overnight. The DMF is distilled off and the residue is precipitated with ether, filtered and washed by boiling with ethanol. Yield 1.6 g (80%); m.p. 199°–200° C. (decompn.); $[\alpha]_D^{27}-28.2°$ (c=0.5, 50% acetic acid).

Elemental analysis, for $C_{43}H_{68}O_{16}N_{10} \cdot H_2O$: Calcd. C, 51.69; H, 7.06; N, 14.02. Found C, 51.59; H, 7.01; N, 13.94.

(VII) Production of Cbz-Ala-Lys(Boc)-Ser-Gln-(D)-Ala-Gly-Ser-Asn-OBu$^t$

In 50 ml of 10% aqueous methanol is dissolved 1.37 g (1.4 m mols) of Cbz-Lys(Boc)-Ser-Gln-(D)-Ala-Gly-Ser-Asn-OBu$^t$ and catalytic reduction is carried out with palladium black as the catalyst. The catalyst is filtered off, the filtrate concentrated and the residue dissolved in 10 ml of DMF. To this solution is added 592 mg (1.5 m mols) of Cbz-Ala-ONB and the mixture is stirred at room temperature overnight. The DMF is distilled off and the residue is precipitated with ether and recovered by filtration. Yield 1.3 g (87%); m.p. 227°–229° C. (decompn.); $[\alpha]_D^{27}-34.4°$ (c=0.5, 50% acetic acid); $Rf^2=0.46$.

Elemental analysis, for $C_{46}H_{73}O_{17}N_{11} \cdot H_2O$: Calcd. C, 51.62; H, 7.06; N, 14.40. Found C, 51.83; H, 7.12; N, 14.60.

(VIII) Production of pGlu-Ala-Lys(Boc)-Ser-Gln-(D)-Ala-Gly-Ser-Asn-OBu$^t$

In 50 ml of aqueous methanol is dissolved 1.3 g (1.2 m mols) of Cbz-Ala-Lys(Boc)-Ser-Gln-(D)-Ala-Gly-Ser-Asn-OBu$^t$ and catalytic reduction is carried out with palladium black as the catalyst. The catalyst is filtered off, the solvent is distilled off and the residue is dissolved in 10 ml of DMF. To this solution is added pGlu-ONB [prepared from 185 mg of pGlu-OH and 267 mg of HONB by the DCC process] and the mixture is stirred at room temperature overnight. The DMF is distilled off and the residue is precipitated with ether, recovered by filtration and washed by boiling with ethanol. Yield 1.0 g (80%); m.p. 230°–232° C. (decompn.); $[\alpha]_D^{27}-40.0°$ (c=0.5, 50% acetic acid); $Rf^2=0.23$.

Elemental analysis, for $C_{43}H_{72}O_{17}N_{12} \cdot 2H_2O$: Calcd. C, 48.48; H, 7.00; N, 15.78. Found C, 48.68; H, 7.23; N, 15.70.

(IX) Production of pGlu-Ala-Lys-Ser-Gln-(D)-Ala-Gly-Ser-Asn-OH

In 5 ml of trifluoroacetic acid is dissolved 500 mg of pGlu-Ala-Lys(Boc)-Ser-Gln-(D)-Ala-Gly-Ser-Asn-OBu$^t$ and the solution is allowed to stand at room temperature for 40 minutes. The trifluoroacetic acid is distilled off and the residue is precipitated with ether and recovered by filtration. The powdery product is dissolved in 50 ml of water and the solution is passed through a column of Amberlite IRA-410 (acetate-form) (2×5 cm). The effluent is combined with washings and lyophilized. The powdery lyophilizate is dissolved in a small amount of 0.1 N-acetic acid and put onto a column of Sephadex LH-20 (2.5×125 cm), elution being carried out with 0.1 N-acetic acid. The fractions from 185 ml through 202 ml are pooled and lyophilized. Yield 170 mg (34%); $[\alpha]_D^{27}-50.6°$ (c=0.42, $H_2O$); $Rf^4$ (Avicel)=0.25; amino acid analysis (acid hydrolyzate); Lys, 1.00(1); Asp, 0.96(1); Ser, 1.77(2); Glu, 2.02(2); Gly, 1.04(1); Ala, 1.95(2); average recovery 75%.

EXAMPLE 5

Production of pGlu-Ala-Lys-Ser-Gln-(D)-Leu-Gly-Ser-Asn-OH (I) Production of Cbz-Gln-(D)-Leu-Gly-OBu$^t$ To a dioxane solution of 1.43 g (0.011 mol) of H-Gly-OBu$^t$ is added 4.26 g (0.01 mol) of Cbz-(D)-Leu-ONB and the mixture is stirred for 12 hours. The solvent is distilled off and the residue is dissolved in ethyl acetate.

The ethyl acetate layer is washed with 10% aqueous citric acid and 5% aqueous sodium hydrogen carbonate. After drying, the solvent is distilled off and the residue is washed well with petroleum benzin.

It is then dissolved in 50 ml of methanol and catalytic reduction is carried out with palladium black as the catalyst. The catalyst is filtered off, the filtrate is concentrated and the oily residue is dissolved in 20 ml of DMF. To this solution are added 2.52 g (0.009 mol) of Cbz-Gln-OH and 1.61 g (0.009 mol) of HONB. Then, under cooling at 0° C., 1.86 g (0.009 mol) of DCC is added, followed by stirring for 48 hours. The byproduct dicyclohexylurea is filtered off and the filtrate concentrated. The residue is precipitated by the addition of ether and the resulting powders are collected by filtration and recrystallized from ethyl acetate, acetonitrile and water in that order. Yield 1.90 g (37.5%); m.p. 184°-185° C. (decompn.); $[\alpha]_D^{22} + 13.3°$ (c=0.5, DMF); $Rf^1 = 0.67$ Elemental analysis, for $C_{25}H_{38}O_7N_4 \cdot \frac{1}{2}H_2O$: Calcd. C, 58.23; H, 7.63; N, 10.87. Found C, 58.58; H, 7.54; N, 11.10.

(II) Production of Cbz-Ser-Gln-(D)-Leu-Gly-OBu$^t$

In 100 ml of methanol is dissolved 1.82 g (3.6 m mols) of Cbz-Gln-(D)-Leu-Gly-OBu$^t$, and in the presence of 684 mg (3.6 m mols) of p-toluenesulfonic acid, catalytic reduction is carried out with palladium black as the catalyst. The catalyst is filtered off, the filtrate concentrated and the concentrate dissolved in 20 ml of DMF. The solution is neutralized with 0.5 ml of triethylamine under icecooling.

To this solution is added a tetrahydrofuran solution of Cbz-Ser-ONB [prepared from 957 mg (4.0 m mols) of Cbz-Ser-OH and 717 mg (4.0 m mols) of HONB by the DCC process] and the mixture is stirred at room temperature for 48 hours. The solvent is distilled off and the residue is precipitated with ether, recovered by filtration and recrystallized from ethanol. Yield 1.1 g (51.4%); m.p. 175°-176° C. (decompn.); $[\alpha]_D^{22} + 2.7°$ (c=0.4, DMF); $Rf^1 = 0.25$.

Elemental analysis, for $C_{28}H_{43}O_9N_5 \cdot \frac{1}{2}H_2O$: Calcd. C, 55.80; H, 7.36; N, 11.62. Found C, 55.86; H, 7.39; N, 11.68.

(III) Production of Cbz-Ser-Gln-(D)-Leu-Gly-OH

In 12 ml of trifluoroacetic acid is dissolved 1.10 g (1.85 m mols) of Cbz-Ser-Glu-(D)-Leu-Gly-OBu$^t$ and the solution is allowed to stand at room temperature for an hour. The trifluoroacetic acid is distilled off under reduced pressure, ether is added to the residue, and the resulting precipitate is collected by filtration and reprecipitated from ethyl acetate. Yield 994 mg (100%); m.p. 201°-205° C. (decompn.); $[\alpha]_D^{22} + 2.1°$ (c=0.5, DMF); $Rf^1 = 0.01$; $Rf^2 = 0.17$.

Elemental analysis, for $C_{24}H_{35}O_9N_5 \cdot H_2O$: Calcd. C, 51.87; H, 6.71; N, 12.61. Found C, 51.89; H, 6.43; N, 12.62.

(IV) Production of Cbz-Ser-Gln-(D)-Leu-Gly-Ser-Asn-OBu$^t$

In 50 ml of methanol is dissolved 688 mg (1.68 m mols) of Cbz-Ser-Asn-OBu$^t$ and catalytic reduction is carried out with palladium black as the catalyst. The catalyst is filtered off and 903 mg (1.68 m mols) of Cbz-Ser-Gln-(D)-Leu-Gly-OH is added to the filtrate. The methanol is distilled off under reduced pressure and the residue is dissolved in 15 ml of DMF. To this solution is added 573 mg (3.36 m mols) of HONB, and at 0° C., 396 mg (2 m mols) of DCC is added. The mixture is stirred at room temperature for 48 hours. The byproduct dicyclohexylurea is filtered off, the filtrate is concentrated and the residue is precipitated with ether, recovered by filtration and recrystallized from ethanol. Yield 1.10 g (82.1%); m.p. 192°-194° C. (decompn.); $[\alpha]_D^{22} - 26.7°$ (c=0.5, 50% acetic acid); $Rf^2 = 0.45$; $Rf^6 = 0.57$. Elemental analysis, for $C_{35}H_{54}O_{13}N_8 \cdot \frac{1}{2}H_2O$: Calcd. C, 52.29; H, 6.90; N, 13.94. Found C, 52.31; H, 6.86; N, 13.84.

(V) Production of Cbz-Lys(Boc)-Ser-Gln-(D)-Leu-Gly-Ser-Asn-OBu$^t$

In 50 ml of a 7:3 mixture of ethanol and water, there is dissolved 1.03 g (1.3 m mols) of Cbz-Ser-Gln-(D)-Leu-Gly-Ser-Asn-OBu$^t$, and catalytic reduction is carried out with palladium black as the catalyst. The catalyst is filtered off and Cbz-Lys(Boc)-OH [prepared from 803 mg (1.43 m mols) of Cbz-Lys(Boc)-OH.DCHA] is added to the filtrate. The mixture is concentrated under reduced pressure and the residue is dissolved in 20 ml of DMF. To this solution is added 256 mg (1.43 m mols) of HONB, and under ice-cooling, 295 mg (1.43 m mols) of DCC is added. The mixture is stirred at room temperature for 48 hours. The byproduct dicyclohexylurea is filtered off, the filtrate is concentrated and the residue is precipitated with ether, collected by filtration and recrystallized from ethanol. Yield 1.0 g (75.2%); m.p. 208°-209° C. (decompn.); $[\alpha]_D^{22} - 27.0°$ (c=0.6, 50% acetic acid); $Rf^2 = 0.51$; $Rf^6 = 0.61$.

Elemental analysis, for $C_{46}H_{74}O_{16}N_{10} \cdot \frac{1}{2}H_2O$: Calcd. C, 53.52; H, 7.32; N, 13.57. Found C, 53.36; H, 7.30; N, 13.59.

(VI) Production of Cbz-Ala-Lys(Boc)-Ser-Gln-(D)-Leu-Gly-Ser-Asn-OBu$^t$

In 30 ml of a 7:3 mixture of ethanol and water, there is dissolved 460 mg (0.45 m mol) of Cbz-Lys(Boc)-Ser-Gln-(D)-Leu-Gly-Ser-Asn-OBu$^t$, and catalytic reduction is carried out with palladium black as the catalyst. The catalyst is filtered off, 112 mg (0.5 m mol) of Cbz-Ala-OH is added to the filtrate and the solvent is distilled off under reduced pressure. The residue is dissolved in 15 ml of DMF and 90 mg of HONB is added. Then, 103 mg (0.5 m mol) of DCC is added under ice-cooling and the mixture is stirred at room temperature for 48 hours. The byproduct dicyclohexylurea is filtered off and the filtrate is concentrated. The residue is precipitated by the addition of ether, recovered by filtration and recrystallized from ethanol. Yield 380 mg (77.2%); m.p. 203°-204° C. (decompn.); $[\alpha]_D^{22} - 34.0°$ (c=0.3, 50% acetic acid); $Rf^2 = 0.50$; $Rf^6 = 0.61$ Elemental analysis, for $C_{49}H_{79}O_{17}N_{11} \cdot H_2O$: Calcd. C, 52.91; H, 7.34; N, 13.85. Found C, 52.84; H, 7.23; N, 13.85.

(VII) Production of pGlu-Ala-Lys(Boc)-Ser-Gln-(D)-Leu-Gly-Ser-Asn-OBu$^t$

In 50 ml of a 7:3 mixture of ethanol and water is dissolved 252 mg (0.23 m mols) of Cbz-Ala-Lys(Boc)-Ser-Gln-(D)-Leu-Gly-Ser-Asn-OBu$^t$ and catalytic reduction is carried out with palladium black as the catalyst. The catalyst is filtered off and 34 mg (0.264 m mol) of pGlu-OH is added to the filtrate and the solvent is distilled off under reduced pressure. The residue is dissolved in 5 ml of DMF and, then, 47 mg (0.264 m mol) of HONB is added. Then, 54 mg (0.264 m mol) of DCC is added under ice-cooling and the mixture is stirred at room temperature for 48 hours. To the reaction mixture is added ether and the resulting precipitate is recovered by filtration and recrystallized from ethanol. Yield 240 mg (97.6%); m.p. 207°-208° C. (decompn.);

$[\alpha]_D^{22} -39.3°$ (c=0.4, 50% acetic acid); $Rf^2=0.24$; $Rf^6=0.45$.

Elemental analysis, for $C_{46}H_{78}O_{17}N_{12} \cdot H_2O$: Calcd. C, 50.72; H, 7.40; N, 15.42. Found C, 50.21; H, 7.37; N, 15.13.

(VIII) Production of pGlu-Ala-Lys-Ser-Gln-(D)-Leu-Gly-Ser-Asn-OH

In 8 ml of trifluoroacetic acid is dissolved 200 mg of pGlu-Ala-Lys(Boc)-Ser-Gln-(D)-Leu-Gly-Ser-Asn-OBu' and the solution is allowed to stand at room temperature for 60 minutes. The trifluoroacetic acid is distilled off under reduced pressure and the residue is precipitated with ether and recovered by filtration. The powders thus obtained are dissolved in a small amount of water and passed through a column of Amberlite IRA-410 (acetate-form) (1.5×7 cm). The effluent is combined with washings and lyophilized. The powdery lyophilizate is dissolved in a small amount of 1 N-acetic acid and put onto a chromatographic column of Sephadex LH-20(2.5×125 cm), elution being carried out with 1 N-acetic acid. The fractions from 190–205 ml are pooled and lyophilized. Yield 65 mg; $[\alpha]_D^{22}-45.4°$ (c=0.4, $H_2O$); $Rf^4$ (Avicel)=0.37; amino acid analysis (acid hydrolyzate): Lys, 1.04(1); Asp, 0.98(1); Ser, 1.86 (2); Glu, 2.14(2); Gly, 0.93(1); Ala, 1.00(1); Leu, 1.00 (1); average recovery, 71.2%.

The same procedure as Example 5 is repeated except that Cbz-(D)-Phe-ONB is used in lieu of Cbz-(D)-Leu-ONB. By this procedure is obtained pGlu-Ala-Lys-Ser-Gln-(D)-Phe-Gly-Ser-Asn-OH.

EXAMPLE 6

Production of pGlu-(D)-Ala-Lys-Ser-Gln-(D)-Leu-Gly-Ser-Asn-OH (I) Production of Cbz-(D)-Ala-Lys(Boc)-Ser-Gln-(D)-Leu-Gly-Ser-Asn-OBu'

In 30 ml of a 7:3 mixture of ethanol and water is dissolved 460 mg (0.45 m mol) of Cbz-Lys(Boc)-Ser-Gln-(D)-Leu-Gly-Ser-Asn-OBu' and catalytic reduction is carried out with palladium black as the catalyst. The catalyst is filtered off, 112 mg (0.5 m mol) of Cbz-(D)-Ala-OH is added and the solvent is distilled off under reduced pressure. The residue is dissolved in 15 ml of DMF and, then, 90 mg (0.5 m mol) of HONB is added. Then, 103 mg (0.5 m mol) of DCC is added and the mixture is stirred at room temperature for 48 hours. To the reaction mixture is added ether and the resulting precipitate is recovered by filtration and recrystallized from ethanol. Yield 400 mg (81.3%); m.p. 226°–227° C. (decompn.); $[\alpha]_D^{22}-17.3°$(c=0.45, 50% acetic acid); $Rf^2=0.51$; $Rf^6=0.65$.

Elemental analysis, for $C_{49}H_{79}O_{17}N_{11} \cdot \frac{1}{2}H_2O$ Calcd. C, 53.34; H, 7.31; N, 13.97. Found C, 53.34; H, 7.44; N, 13.86.

(II) Production of pGlu-(D)-Ala-Lys(Boc)-Ser-Gln-(D)-Leu-Gly-Ser-Asn-OBu'

In 80 ml of a 7:3 mixture of ethanol and water is dissolved 372 mg (0.34 m mol) of Cbz-(D)-Ala-Lys(Boc)-Ser-Gln-(D)-Leu-Gly-Ser-Asn-OBu' and catalytic reduction is carried out at 40° C. with palladium black as the catatlyst. The catalyst is filtered off, 48 mg (0.374 m mol) of pGlu-OH is added to the filtrate and the solvent is distilled off under reduced pressure. The residue is dissolved in DMF and 67 mg (0.374 m mol) of HONB is added. Then, under ice-cooling, 77 mg (0.374 m mol) of DCC is added and the mixture is stirred at room temperature for 48 hours. To this reaction mixture is added ether and the resulting precipitate is recovered by filtration and recrystallized from ethanol. Yield 330 mg (90.7%); m.p.203°–204° C. (decompn.); $[\alpha]_D^{22}-17.0°$(c=0.4, 50% acetic acid); $Rf^2=0.24$; $Rf^6=0.45$.

Elemental analysis, for $C_{46}H_{78}O_{17}N_2$: Calcd. C, 50.72; H, 7.40; N, 15.42. Found C, 50.75; H, 7.76; N, 15.29.

(III) Production of pGlu-(D)-Ala-Lys-Ser-Gln-(D)-Leu-Gly-Ser-Asn-OH

In 14 ml of trifluoroacetic acid is dissolved 300 mg of pGlu-(D)-Ala-Lys(Boc)-Ser-Gln-(D)-Leu-Gly-Ser-Asn-OBu' and the solution is allowed to stand at room temperature for 60 minutes. The trifluoroacetic acid is distilled off under reduced pressure and the residue is precipitated with ether and recovered by filtration. The powdery precipitate is dissolved in a small amount of water and the solution is passed through a column of amberlite IRA-410 (acetate-form) (1.5×10.0 cm). The effluent is combined with washings and lyophilized. The powdery lyophilizate is dissolved in a small amount of 1N-acetic acid and the solution is applied to a column of Sephadex LH-20 (2.5×125 cm), elution being carried out with 1N-acetic acid. The fractions from 195 through 210 ml are pooled and lyophilized. Yield 125 mg; $[\alpha]_D^{22}-12.5°$(c=0.19, $H_2O$); $Rf^4$(Avicel)=0.38; amino acid analysis (acid hydrolyzate); Lys, 1.01(1); Asp, 0.88(1); Ser, 1.95(2); Glu, 1.81(2); Gly, 1.18(1); Ala, 1.03(1); Leu, 1.00(1); mean recovery rate 78%.

EXAMPLE 7

Production of pGlu-Ala-Lys-Ser-Gln-Gly-(D)-Leu-Ser-Asn-OH (I) Production of Cbz-(D)-Leu-Ser-Asn-OBu'

In 100 ml of methanol is dissolved 1.2 g (2.9 m mols) of Cbz-Ser-Asn-OBu' and catalytic reduction is carried out with palladium black as the catalyst. The catalyst is filtered off, 50 ml of DMF is added to the filtrate and the methanol is distilled off. To this DMF solution is added 1.2 g of Cbz-(D)-Leu-ONB and the mixture is stirred at room temperature overnight. The DMF is distilled off, the residue is extracted with 100 ml of ethyl acetate, washed with 5% aqueous sodium hydrogen carbonate and dried over anhydrous sodium sulfate. The ethyl acetate is distilled off and the residue is precipitated with ether and recrystallized from ethyl acetate-petroleum benzin. Yield 1.0 g (67%); m.p.171°–172° C.; $[\alpha]_D^{23}-2.7°$(c=0.34, DMF); $Rf^2=0.42$.

Elemental analysis, for $C_{25}H_{38}O_8N_4$: Calcd. C, 57.45; H, 7.33; N, 10.72. Found C, 57.40; H, 7.24; N, 10.50.

(II) Production of Cbz-Ser-Gln-Gly-(D)-Leu-Ser-Asn-OBu'

Using 628 mg (1.2 m mols) of Cbz-(D)-Leu-Ser-Asn-OBu' and 510 mg of Cbz-Ser-Gln-Gly-OH, the same procedure as Example 1-(IV) is followed to obtain the indicated compound. Yield 850 mg (87%); m.p.180°–181° C.; $[\alpha]_D^{23}-8.4$ (c=0.3, 50% acetic acid); $Rf^2=0.40$.

Elemental analysis, for $C_{35}H_{54}O_{13}N_8 \cdot H_2O$ Calcd. C, 51.71; H, 6.94; N, 13.78. Found C, 51.60; H, 7.02; N, 13.51.

(III) Production of Cbz-Lys(Boc)-Ser-Gln-Gly-(D)-Leu-Ser-Asn-OBu'

Using 0.79 g (1.0 m mol) of Cbz-Ser-Gln-Gly-(D)-Leu-Ser-Asn-OBu' and 0.65 g of Cbz-Lys(Boc)-ONB, the same procedure as Example 1-(V) is followed to synthesize the above-indicated compound. Yield 920 mg (88%); m.p.189°–190° C.; $[\alpha]_D^{23}-16.6°$(c=0.32; 50% acetic acid); $Rf^2=0.62$ Elemental analysis, for $C_{46}H_{74}O_{16}N_{10}.H_2O$: Calcd. C, 53.06; H, 7.35; N, 13.45. Found C, 52.88; H, 7.21; N, 13.20.

(IV) Production of Cbz-Ala-Lys(Boc)-Ser-Gln-Gly-(D)-Leu-Ser-Asn-OBu$^t$

Using 0.90 g (0.9 m mol) of Cbz-Lys(Boc)-Ser-Gln-Gly-(D)-Leu-Ser-Asn-OBu$^t$ and 0.38 g of Cbz-Ala-ONB, the same procedure as Example 1-(VI) is followed to prepare the above-identified compound. Yield 0.70 g (72%); m.p.192°–193° C. (decompn.); $[\alpha]_D^{23} -23.1°(c=0.29, 50\%$ acetic acid); $Rf^2=0.49$.

Elemental analysis, for $C_{49}H_{79}O_{17}N_{11}.H_2O$: Calcd. C, 52.91; H, 7.29; N, 13.84. Found C, 52.75; H, 7.21; N, 13.66.

(V) Production of pGlu-Ala-Lys(Boc)-Ser-Gln-Gly-(D)-Leu-Ser-Asn-OBu$^t$

Using 0.65 g (0.6 m mol) of Cbz-Ala-Lys(Boc)-Ser-Gln-Gly-(D)-Leu-Ser-Asn-OBu$^t$ and 0.21 of pGlu-ONB, the same procedure as Example 1-(VII) is followed to prepare the above-indicated compound. Yield 0.52 g (80%); m.p. 194°–195° C. (decompn.); $[\alpha]_D^{23} -31.0°(c=0.36, 50\%$ acetic acid); $Rf^2=0.25$ Elemental analysis, for $C_{46}H_{78}O_{17}N_{12}.H_2O$: Calcd. C, 50.72; H, 7.40; N, 15.43. Found C, 50.59; H, 7.19; N, 15.19.

(VI) Production of pGlu-Ala-Lys-Ser-Gln-Gly-(D)-Leu-Ser-Asn-OH 450 mg of pGlu-Ala-Lys(Boc)-Ser-Gln-Gly-(D)-Leu-Ser-Asn-OBu$^t$ is treated with 5 ml of trifluoroacetic acid at room temperature for 40 minutes and the reaction product is purified as in Example 1-(VIII). Yield 260 mg (58%); $[\alpha]_D^{23} -40.0°$ (c=0.31, $H_2O$); $Rf^4$(Avicel)=0.23, amino acid analysis (hydrolyzed with HCl); Lys, 0.95(1); Asp, 0.92(1); Ser, 1.79(2); Glu, 2.05(2); Gly, 1.01(1); Ala, 1.05(1); Leu, 1.05(1); average recovery 81%.

EXAMPLE 8

Production of pGlu-Ala-Lys-Ser-Gln-(D)-Phe-Gly-Ser-Asn-OH (I) Production of Cbz-Gln-(D)-Phe-Gly-OBu$^t$ Using 6.91 g (15 m mols) of Cbz-(D)-Phe-ONB, 2.56 g (19.5 m mols) of H-Gly-OBu$^t$ and 3.36 g (12 m mols) of Cbz-Gln-OH, the same procedure as Example 5-(I) is followed to prepare the above-indicated compound. Yield 3.30 g (40.8%); m.p. 180°–181° C. (decompn.); $[\alpha]_D^{25} +10.7°(c=0.5, DMF)$, $Rf^1=0.55$ Elemental analysis, for $C_{28}H_{36}O_7N_4$ Calcd. C, 62.20; H, 6.71; N, 10.36. Found C, 61.99; H, 6.85; N, 10.51.

(II) Production of Cbz-Ser-Gln-(D)-Phe-Gly-OBu$^t$

Using 2.87 g (5.3 m mols) of Cbz-Gln-(D)-Phe-Gly-OBu$^t$ and 1.39 g (5.8 m mols) of Cbz-Ser-OH, the same procedure as Example 5-(II) is followed to prepare the above-indicated compound. Yield 1.5 g (45.2%); m.p. 179°–180° C. (decompn.); $[\alpha]_D^{25} +2.5°(c=0.5, DMF)$: $Rf^1=0.17$, $Rf^2=0.93$.

Elementary analysis, for $C_{31}H_{41}O_9N_5$: Calcd. C, 59.32; H, 6.58; N, 11.16. Found C, 58.88; H, 6.54; N, 11.14.

(III) Production of Cbz-Ser-Gln-(D)-Phe-Gly-OH

Using 1.4 g (2.23 m mols) of Cbz-Ser-Gln-(D)-Phe-Gly-OBu$^t$, the same procedure as Example 5-(III) is followed to prepare the above-indicated compound. Yield 1.25 g (98.4%); m.p. 210°–211° C. (decompn.); $[\alpha]_D^{25} +2.2°(c=0.5, DMF)$; $Rf^2=0.28$.

Elemental analysis, for $C_{27}H_{33}O_9N_5.H_2O$: Calcd. C, 55.00; H, 5.98; N, 11.88. Found C, 54.99; H, 5.71; N, 11.94.

(IV) Production of Cbz-Ser-Gln-(D)-Phe-Gly-Ser-Asn-OBu$^t$

Using 860 mg (2.1 m mols) of Cbz-Ser-Asn-OBu$^t$ and 1.20 g (2.1 m mols) of Cbz-Ser-Gln-(D)-Phe-Gly-OH, the same procedure as Example 5-(IV) is followed to prepare the above-indicated compound. Yield 1.50 g (86.2%); m.p. 201°–202° C. (decompn.); $[\alpha]_D^{25} -25.3°(c=0.5, 50\%$ acetic acid); $Rf^6=0.58$ Elemental analysis, for $C_{38}H_{52}O_{13}N_8$: Calcd. C, 55.06; H, 6.32; N, 13.52. Found C, 54.66; H, 6.31; N, 13.53.

(V) Production of Cbz-Lys(Boc)-Ser-Gln-(D)-Phe-Gly-Ser-Asn-OBu$^t$

Using 1.41 g (1.7 m mols) of Cbz-Ser-Gln-(D)-Phe-Gly-Ser-Asn-OBu$^t$ and 1.05 g (1.87 m mols) of Cbz-Lys(Boc)-OH.DCHA, the same procedure as Example 5-(V) is followed to prepare the above-indicated compound. Yield 1.66 g. (92.2%); m.p. 209°–210° C. (decompn.); $[\alpha]_D^{24} -25.0°(c=0.5, 50\%$ acetic acid); $Rf^6=0.62$.

Elemental analysis, for $C_{49}H_{72}O_{16}N_{10}$: Calcd. C, 55.67; H, 6.87; N, 13.25. Found C, 55,44; H, 6.88; N, 13.28.

(VI) Production of Cbz-Ala-Lys(Boc)-Ser-Gln-(D)-Phe-Gly-Ser-Asn-OBu$^t$

In 50 ml of a 7:3 mixture of ethanol and water is dissolved 793 mg (0.75 m mol) of Cbz-Lys(Boc)-Ser-Gln-(D)-Phe-Gly-Ser-Asn-OBu$^t$, and in the presence of 0.045 ml (0.75 m mol) of acetic acid, catalytic reduction is carried out with palladium black as the catalyst. The catalyst is filtered off, and the filtrate is concentrated. The residue is dissolved in 15 ml of DMF, 288 mg (0.90 m mol) of Cbz-Ala-OSu is added and the mixture is stirred at room temperature for 48 hours. The reaction mixture is concentrated and to the residue is added ether. The resulting precipitate is recovered as powder by filtration and recrystallized from ethanol. Yield 730 mg (86.3%); m.p. 213°–214° C. (decompn.); $[\alpha]_D^{24} -30.3°(c=0.4, 50\%$ acetic acid); $Rf^6=0.73$.

Elemental analysis, for $C_{52}H_{77}O_{17}N_{11}.H_2O$: Calcd. C, 54.48; H, 6.95; N, 13.44. Found C, 54.42; H, 6.88; N, 13.54.

(VII) Production of pGlu-Ala-Lys(Boc)-Ser-Gln-(D)-Phe-Gly-Ser-Asn-OBu$^t$

Using 677 mg (0.6 m mol) of Cbz-Ala-Lys(Boc)-Ser-Gln-(D)-Phe-Gly-Ser-Asn-OBu$^t$ and 85 mg (0.66 m mol) of pGlu-OH, the same procedure as Example 5-(VII) is followed to prepare the above-indicated compound. Yield 610 mg (92.4%); m.p. 216°–217° C. (decompn.); $[\alpha]_D^{25} -37.3°(c=0.4, 50\%$ acetic acid); $Rf^6=0.53$.

Elemental analysis, for $C_{49}H_{76}O_{17}N_{17}.H_2O$: Calcd. C, 52.40; H, 7.00; N, 14.97. Found C, 52.32; H, 7.13; N, 14.85.

(VIII) Production of pGlu-Ala-Lys-Ser-Gln-(D)-Phe-Gly-Ser-Asn-OH

Using 500 mg of pGlu-Ala-Lys(Boc)-Ser-Gln-(D)-Phe-Gly-Ser-Asn-OBu$^t$ and 15 ml of trifluoroacetic acid, the same procedure as Example 5-(VIII) is followed to prepare the above-identified compound. Yield 280 mg; $[\alpha]_D^{24} -51.7°(c=0.2,$ water), $Rf^4$(Avicel)=0.35; amino acid analysis (hydrolyzed with HCl); Lys, 1.00(1); Asp, 0.70(1); Ser, 2.02(2); Glu, 2.03(2); Gly, 1.02(1); Ala, 0.77(1); Phe, 1.01(1); average recovery 84.5%.

EXAMPLE 9

Production of
pGlu-Ala-Lys-Ser-Gln-(D)-Ser-Gly-Ser-Asn-OH (I) Production of Cbz-Gln-(D)-Ser-Gly-OBu'

Using 2.39 g (0.01 mol) of Cbz-(D)-Ser-OH, 1.97 g (0.015 mol) of H-Gly-OBu' and 2.80 g (0.01 mol) of Cbz-Gln-OH, the same procedure as Example 5-(I) is followed to prepare the above-indicated compound. Yield 2.4 g (50.0%); m.p. 167°–168°C.; $[\alpha]_D^{24}+2.2°(c=0.4, DMF)$; $Rf^1=0.13$.

Elemental analysis, for $C_{22}H_{32}O_8N_4$: Calcd. C, 54.99; H, 6.71; N, 11.66. Found C, 54.66; H, 6.80; N, 11.66.

(II) Production of Cbz-Ser-Gln-(D)-Ser-Gly-OBu'

Using 2.31 g (4.8 m mols) of Cbz-Gln-(D)-Ser-Gly-OBu' and 1.26 g (5.28 m mols) of Cbz-Ser-OH, the same procedure as Example 5-(II) is followed to prepare the above-indicated compound. Yield 1.86 g (68.4%); m.p. 163°–164° C. (decompn.); $[\alpha]_D^{24}-4.9°(c=0.5, DMF)$; $Rf^1=0.08$ Elemental analysis, for $C_{31}H_{41}O_9N_5$: Calcd. C, 59.32; H, 6.58; N, 11.16. Found C, 58.88; H, 6.54; N, 11.14.

(III) Production of Cbz-Ser-Gln-(D)-Ser-Gly-OH

Using 1.6 g (2.82 m mols) of Cbz-Ser-Gln-(D)-Ser-Gly-OBu', the same procedure as Example 5-(III) is followed to prepare the above-indicated compound. Yield 1.35 g (93.8%); m.p. 164°–165° C. (decompn.); $[\alpha]_D^{24}-4.8°(c=0.5, DMF)$; $Rf^6=0.06$.

(IV) Production of Cbz-Ser-Gln-(D)-Ser-Gly-Ser-Asn-OBu'

Using 1.15 g (2.8 m mols) of Cbs-Ser-Asn-OBu' and 1.43 g (2.8 m mols) of Cbz-Ser-Gln-(D)-Ser-Gly-OH, the same procedure as Example 5-(IV) is followed to prepare the above-indicated compound. Yield 1.80 g (83.7%); m.p. 193°–195° C. (decompn.); $[\alpha]_D^{24}-25.2°(c=0.5, 50\%$ acetic acid); $Rf^6=0.29$.

Elemental analysis, for $C_{32}H_{48}O_{14}N_8\cdot H_2O$: Calcd. C, 48.85; H, 6.40; N, 14.24. Found C, 48.60; H, 6.44; N, 14.30.

(V) Production of Cbz-Lys(Boc)-Ser-Gln-(D)-Ser-Gly-Ser-Asn-OBu'

Using 1.69 g; (2.2 m mols) of Cbz-Ser-Gln-(D)-Ser-Gly-Ser-Asn-OBu' and 1.36 g (2.42 m mols) of Cbz-Lys(Boc)-OH.DCHA, the same procedure as Example 5-(V) is followed to prepare the above-indicated compound. Yield 2.02 g. (92.2%); m.p. 197°–199° C. (decompn.); $[\alpha]_D^{24}-25.7°(c=0.5, 50\%$ acetic acid); $Rf^6=0.44$.

Elemental analysis, for $C_{43}H_{68}O_{17}N_{10}\cdot H_2O$: Calcd. C, 50.88; H, 6.95; N, 13.80. Found C, 51.06; H, 7.17; N, 13.83.

(VI) Production of Cbz-Ala-Lys(Boc)-Ser-Gln-(D)-Ser-Asn-OBu'

Using 997 mg (1 m mol) of Cbz-Lys(Boc)-Ser-Gln-(D)-Ser-Gly-Ser-Asn-OBu' and 384 mg (1.2 m mol) of Cbz-Ala-OSu, the same procedure as Example 8-(VII) is followed to prepare the above-indicated compound. Yield 920 mg (86.1%); m.p. 202°–204° C. (decompn.); $[\alpha]_D^{24}-32.2°(c=0.4, 50\%$ acetic acid); $Rf^6=0.44$.

Elemental analysis, for $C_{46}H_{73}O_{18}N_{11}\cdot H_2O$: Calcd. C, 50.87; H, 6.96; N, 14.18. Found C, 50.75; H, 6.92; N, 14.20.

(VII) Production of pGlu-Ala-Lys(Boc)-Ser-Gln-(D)-Ser-Gly-Ser-Asn-OBu'

Using 801 mg (0.75 m mol) of Cbz-Ala-Lys(Boc)-Ser-Gln-(D)-Ser-Gly-Ser-Asn-OBu' and 107 mg (0.825 m mol) of pGlu-OH, the same procedure as Example 5-(VII) is followed to prepare the above-indicated compound. Yield 650 mg (83.0%); m.p. 230°–231° C. (decompn.); $[\alpha]_D^{25}-38.1°(c=0.5, 50\%$ acetic acid); $Rf^6=0.19$.

Elemental analysis, for $C_{43}H_{72}O_{18}N_{12}\cdot 2H_2O$: Calcd. C, 47.77; H, 7.08; N, 15.54. Found C, 47.93; H, 7.07; N, 15.57.

(VIII) Production of pGlu-Ala-Lys-Ser-Gln-(D)-Ser-Gly-Ser-Asn-OH

Using 550 mg of pGlu-Ala-Lys(Boc)-Ser-Gln-(D)-Ser-Gly-Ser-Asn-OBu' and 20 ml of trifluoroacetic acid, the same procedure as Example 5-(VIII) is followed to prepare the above-indicated compound. Yield 320 mg; $[\alpha]_D^{24}-56.3°(c=0.5,$ water); $Rf^4(Avicel)=0.17$; amino acid analysis (hydrolyzed with HCl); Lys, 1.10(1); Asp, 1.00(1); Ser, 3.02(3); Glu, 2.14(2); Gly, 1.10(1); Ala, 1.00(1); average recovery 87.0%.

EXAMPLE 10

Injection

Composition:

| (1) | pGlu—Ala—Lys—Ser—Gln—(D)-Leu—Gly—Ser—Asn—OH | 1000 mg |
|---|---|---|
| (2) | Saline a sufficient quantity to make | 1000 ml |

Preparation:

(1) is dissolved in (2)

One milliliter each of the solution is used to fill 1,000 ampoules and the air within the ampoules is replaced with nitrogen gas, then the ampoule is sealed and stocked in the referigerator. All the processes are conducted under sterile conditions.

EXAMPLE 11

Injection

Composition:

| (1) | pGlu—Ala—Lys—Ser—Gln—(D)-Ala—Gly—Ser—Asn—OH | 1000 mg |
|---|---|---|
| (2) | D-Mannitol | 20 g |
| (3) | Distilled water, a sufficient quantity to make | 1000 ml |

Preparation:

(1) and (2) are dissolved in (3)

One milliliter each of the solution is used to fill 1000 ampoules and the ampoules are lyophilized. The air within the ampoules is replaced with nitrogen gas, then the ampoules are sealed. All the processes are conducted under sterile conditions.

What we claim is:

1. A nonapeptide of the formula:

pGlu-X-Lys-Ser-Gln-Y-Z-Ser-Asn-OH wherein X is Ala or (D)-Ala; Y and Z are the same or different and each is the residue of a D-amino acid selected from the group consisting of alanine, leucine, isoleucine, phenylalanine, valine, 2-amino-n-butyric acid, serine, threonine, norleucine, methionine, norvaline and tyrosine, or Gly; and at least one of X, Y and Z is the residue of D-amino acid.

2. A nonapeptide according to claim 1, wherein Y is the residue of a D-amino acid selected from the group consisting of alanine, leucine, isoleucine, phenylalanine, valine, 2-amino-n-butyric acid, serine, threonine, norleucine, methionine, norvaline and tyrosine.

3. A nonapeptide according to claim 1, wherein Y and Z are the same or different and each is (D)-Ala, (D)-Leu, (D)-Phe, (D)Val or Gly.

4. The nonapeptide according to claim 1, wherein X is (D)-Ala, and both of Y and Z are Gly.

5. The nonapeptide according to claim 1, wherein X is Ala, Y is (D)-Ala and Z is Gly.

6. The nonapeptide according to claim 1, wherein X is Ala, Y is Gly and Z is (D)-Ala.

7. The nonapeptide according to claim 1, wherein X is Ala, Y is (D)-Leu and Z is Gly.

8. The nonapeptide according to claim 1, wherein X is (D)-Ala, Y is (D)-Leu and Z is Gly.

9. The nonapeptide according to claim 1, wherein X is Ala, Y is (D)-Phe and Z is Gly.

10. The nonapeptide according to claim 1, wherein X is Ala, Y is (D)-Ser and Z is Gly.

11. A pharmaceutical composition for immuno-regulation which comprises, as an active ingredient, an effective amount of a nonapeptide of the formula:

pGlu-X-Lys-Ser-Gln-Y-Z-Ser-Asn-OH wherein X is Ala or (D)-Ala; Y and Z are the same or different and each is the residue of a D-amino acid selected from the group consisting of alanine, leucine, isoleucine, phenylalanine, valine, 2-amino-n-butyric acid, serine, threonine, norleucine, methionine, norvaline and tyrosine, or Gly; and at least one of X, Y and Z is the residue of D-amino acid, and a pharmaccologically acceptable carrier, excipient or diluent therefor.

* * * * *